US005332765A

United States Patent [19]
Lorentzen et al.

[11] Patent Number: 5,332,765
[45] Date of Patent: Jul. 26, 1994

[54] MICROBICIDAL AGENTS

[75] Inventors: Jens-Peter Lorentzen, Cologne; Georg-Wilhelm Ludwig; Wilfried Paulus, both of Krefeld, all of Fed. Rep. of Germany

[73] Assignee: Bayer Aktiengesellschaft, Leverkusen, Fed. Rep. of Germany

[21] Appl. No.: 988,079

[22] Filed: Dec. 9, 1992

[30] Foreign Application Priority Data

Dec. 19, 1991 [DE] Fed. Rep. of Germany ....... 4141953

[51] Int. Cl.$^5$ ................................................ C09D 5/14
[52] U.S. Cl. .................................. 523/122; 424/78.09; 424/405
[58] Field of Search ...................... 523/122; 424/78.09, 424/405; 514/449

[56] References Cited

U.S. PATENT DOCUMENTS

| | | | |
|---|---|---|---|
| 4,719,227 | 1/1988 | Schade et al. | 514/452 |
| 4,879,310 | 11/1989 | Schade et al. | 514/519 |
| 5,190,580 | 3/1993 | Gruening | 523/122 |

FOREIGN PATENT DOCUMENTS

| | | |
|---|---|---|
| 0199047 | 10/1986 | European Pat. Off. . |
| 0327220 | 8/1989 | European Pat. Off. . |
| 0510458 | 10/1992 | European Pat. Off. . |
| 2723118 | 11/1978 | Fed. Rep. of Germany . |
| 3607624 | 9/1987 | Fed. Rep. of Germany . |
| 1590662 | 5/1970 | France . |
| 2352552 | 12/1977 | France . |
| 2138292 | 10/1984 | United Kingdom . |

Primary Examiner—Paul R. Michl
Assistant Examiner—LaVonda DeWitt
Attorney, Agent, or Firm—Sprung Horn Kramer & Woods

[57] ABSTRACT

There were described microbicidal agents for the protection of aqueous functional fluids which contain, as active substances, a combination of at least one iodopropargyl derivative and benzyl alcohol mono(poly)hemiformal.

11 Claims, No Drawings

MICROBICIDAL AGENTS

The present application relates to microbicidal agents which have an improved bactericidal and fungicidal activity and a broad spectrum of action, characterised in that they contain, as active compounds, iodopropargyl derivatives such as, for example, iodopropargyl N-butyl-carbamate (IPBC) and benzyl alcohol mono(-poly)hemiformal (BHF) and, if appropriate further microbicides.

IPBC is a known fungicide and algicide (U.S. Pat. No. 4,276,211 and GB 2,138,292), which is preferably used in paints. However, in contrast to the fungicidal activity of IPBC, the antibacterial action is less pronounced and incomplete, so that, for example, aqueous paints which contain IPBC as a film fungicide require additional preservation. In general, a broad bactericidal and fungicidal action is crucial for the preservation of industrial materials.

Since iodopropargyls such as IPBC have no pronounced activity in particular against Gram-negative bacteria which are relevant for practical conditions, the active compound on ists own is unsuitable for the preservation of aqueous industrial fluids.

In contrast, BHF has an outstanding action against Gram-positive as well as Gram-negative bacteria, while the fungicidal action is frequently only achieved with higher concentrations. Because of its volatility and solubility in water, BHF is not suitable for a permanent fungicidal protection of coatings. In principle, BHF can be employed in the preservation of aqueous industrial fluids, however, it is necessary to use concentrations in the range of approx. 1000 ppm since the fungicidal properties are less pronounced.

For reasons of economy, toxicological acceptability and ecology, and for reasons regarding compatibility of industrial materials with microbicides, it is recommended that the material to be protected contains microbicides at the lowest possible concentration.

Surprisingly, it has now been found that the new microbicidal agents which contain iodopropargyl derivatives such as, preferably, IPBC, and BHF, not only provide aqueous functional fluids with better fungicidal protection, but also have a better preserving action, even when applied at a concentration which is lower than that of the individual components. Industrial fluids which are preferably preserved are those which are susceptible to bacteria as well as to moulds and attack by yeasts.

The following may preferably be mentioned:
1. Glues and sizes based on the known raw materials of animal, vegetable or synthetic origin.
2. Cooling lubricants which can be subclassified into mineral-oil based, partly-synthetic or fully-synthetic emulsions or solutions.
3. Polymer dispersions such as latex dispersions or dispersions based on other polymers and biopolymers.
4. Solutions, dispersions or slurries of starch, or other starch-based products such as, for example, printing thickeners.
5. Slurries of other raw materials such as pigments (for example iron oxide pigments, carbon black pigments, titanium dioxide pigments), or slurries of fillers such as kaolin or calcium carbonate.
6. Concrete additives, for example those based on melasses or ligninsulphonates.
7. Bituminous emulsions.
8. Functional fluids for the printing industry (for example fount solutions for offset printing).
9. Cleaners and detergents for industrial and domestic use.
10. Mineral oils or mineral oil products (for example diesel fuels).
11. Auxiliaries for the leather, textile or photochemical industries.
12. Precursors and intermediates in the chemical industry, for example in the production and storage of colours.
13. Inks or China inks.
14. Aqueous coatings.
15. Sizes and finishes.
16. Wax and polishing emulsions.
17. Starch solutions.
18. Gelatine preparations.
19. Cosmetics.

Another particularly important aspect is the fact that the active compound combinations, or agents, according to the invention, for example provide aqueous paints not only with fungicidal and algicidal properties (film protection), but also protect them reliably and over a prolonged period in cans or tanks during storage.

Surprisingly, the microbicidal active compound combinations according to the invention display a pronounced synergism, so that the use concentrations can be kept low. In total, the new microbicidal agents represent an enrichment of the prior art.

The ratios by weight of the iodopropargyl compounds to BHF can be varied within a broad range.

In the case of paints, such as dispersion paints, which should also be self-preserving besides being provided with a fungicidal film protection, the iodopropargyl/BHF ratio is between 100:0 to 50:50, preferably 99:1 to 70:30, particularly preferably 95:5 to 80:20.

For the preservation of aqueous industrial fluids where the agent has a broad antimicrobical (bactericidal and fungicidal) activity, the BHF/iodopropargyl ratio should be 100:0 to 50:50, preferably 99:1 to 70:30, particularly preferably 98:2 to 90:10.

The active compound combinations according to the invention have a powerful action against microorganisms. The active compound combinations according to the invention are used in the protection of materials for protecting industrial materials, in particular for the protection of aqueous functional fluids; they are mainly active against moulds, bacteria, as well as against yeasts, algae and slime organisms. The following genera of microorganisms may be mentioned by way of example but without imposing any limitation:

Alternaria, such as *Alternaria tenuis*, Aspergillus, such as *Aspergillus niger* and *Aspergillus terreus*, Aureobasidium, such as *Aureobasidium pullulans*, Chaetomium, such as *Chaetomium globosum*, Cladosporium, such as *Cladosporium herbarum*, Coniophora, such as *Coniophora puteana*, Gliocladium, such as *Gliocladium virens*, Lentinus, such as *Lentinus tigrinus*, Paecilomyces, such as *Paecilomyces varioti*, Penicillium, such as *Penicillium brevicaule*, *Penicillium glaucum* and *Penicillium pinophilum*, Polyporus, such as *Polyporus versicolor*, Sclerophoma, such as *Sclerophoma pityophila*, Streptoverticillium, such as *Streptoverticillium reticulum*, Trichoderma, such as *Trichoderma viride*, Trichophyton, such as *Trichophyton mentagrophytes*;

Escherichia, such as *Escherichia coli*, Pseudomonas, such as *Pseudomonas areuginosa*, Staphylococcus, such as *Staphylococcus aureus*; Candida, such as *Candida albicans*.

The amount of the active compound combinations employed depends on the field of application. The optimum amount to be employed can be determined on application by test series. In general however, 0.001 to 20% by weight, preferably 0.05 to 10% by weight, in particular 0.01 to 2% by weight, of the active compound mixtures relative to the material to be protected, is sufficient.

The new active compound combinations can be incorporated into the aqueous functional fluids as such, in the form of concentrates or generally customary formulations such as powders, granules, solutions, suspensions, emulsions or pastes.

The formulations mentioned are prepared in a manner known per se, for example by mixing the active compounds with a solvent or with diluents, emulsifiers, dispersants and/or binders or fixatives, if appropriate desiccants and UV stabilisers and if appropriate colours and pigments and other processing auxiliaries.

Suitable solvents or diluents are organochemical solvents or solvent mixtures.

A preferred, suitable solvent or diluent is water, if appropriate as a mixture with one or more of the solvents or diluents, emulsifiers and dispersants which are customarily used.

The activity and the spectrum of action of the active compound combination according to the invention or of the agents, concentrates or, generally, formulations prepared therewith, is increased if, if appropriate, other antimicrobially active substances, fungicides, insecticides or other active compounds are added to widen the spectrum of the active compound or to achieve specific effects such as, for example, an additional protection against insects. Examples of particularly advantageous components are the following compounds:

Sulphenamides such as dichlofluanid (Euparen), tolylfluanid (methyleuparen), folpet, fluorfolpet; thiocyanates such as thiocyanatomethylthiobenzothiazole (TCMTB), methylenebisthiocyanate (MBT); morpholine derivatives such $C_{11}$–$C_{14}$-4-alkyl-2,6-dimethylmorpholine homologues (tridemorph), (±)-cis-4-[3-tert.-butylphenyl)-2-methylpropyl]-2,6-dimethylmorpholine (fenpropimorph), falimorph; tetrachloro-4-methylsulphonylpyridine, metal soaps such as tin naphthenate, copper naphthenate, zinc naphthaenate, tin octoate, copper octoate, zinc octoate, tin 2-ethylhexanoate, copper 2-ethylhexanoate, zinc 2-ethylhexanoate, zinc olet, copper olet, zinc olet, tin phosphate, copper phosphate, zinc phosphate, tin benzoate, copper benzoate, zinc benzoate, tri-butyl-tin oxide (TBTD), copper oxide and zinc oxide; zinc salts of dialkyldithiocarbamates; tetramethylthiuram disulphide (TMTD); 2,4,5,6-tetrachloroisophthalodinitrile (chlorthalonil); benzothiazoles such as 2-mercaptobenzothiazole; thiazolylbenzimidazole; benzimidazolylalkylcarbamates, e.g. carbendazin; quinolines, e.g. 8-hydroxyquinolin and the copper salt thereof; tris-N-(cyclohexyldiazeniumdioxy)-aluminum and N-(cyclohexyldiazeniumdioxy)-tributyltin.

Phenol derivatives such as, for example, p-chloro-m-cresol, p-chloro-m-xylenol; cresols, thymols, 2-benzyl-4-chloro-phenol, o-phenyl-phenol, dichlorophen, tribromophenol.

Aldehydes such as formaldehyde or its depot substances such as, for example, tris-ω-hydroxyethyl-hexahydro-s-triazine, N-methylolchloracetamide, dimethylolurea, oxazolidines, methylenebis-1,3-dimethyloxazolidine, methylenebis-1,3-oxazine, trisoxymethylmethane, tetrahydro-1,3,5-thiadiazine-2-thione as well as glutaric dialdehyde, acrolein and glyoxal.

Isothiazolinones such as, for example, 5-chloro-2-methyl-isothiazolin-3-one, 2-methylisothiazolin-3-one, benzisothiazolinone, N-octylisothiazolinone, cyclopentylisothiazolinone, 4,5-dichloro-N-octyl- or -methyl)-isothiazolin-3-one.

Iodopropargyl alcohol and derivatives such as, for example, iodopropargyl alcohol carbamates I—C≡C—CH$_2$OCONHR where R=H, alkyl or aryl, in particular R=Ph. Esters of iodopropargyl alcohol, in particular with protected or unprotected amino acids, dipeptides and higher peptides, for example I—C≡CC-H$_2$OCH$_2$OCOCHRNHCO$_2$C(CH$_3$)$_3$.

Ethoxylated iodopropargyl alcohols such as, for example, I—C≡C—CH$_2$OCH$_2$CH$_2$OH, triiodoallyl alcohol.

Microbistatically or microbicidally active alcohols such as, for example, benzyl alcohol, methanol, ethanol, isopropanol, phenylethyl alcohol, 2-phenoxyethanol, 2-phenoxy-1-propanol, 3-(4-chlorophenoxy)-1,2-propanediol and 2,4-dichlorobenzyl alcohol.

Bromonitro compounds such as, for example, 2-bromo-2-nitropropane-1,3-diol or 5-bromo-5-nitro-1,3-dioxane.

Organic acids and their derivatives such as, for example, formic acid, acetic acid, chloroacetic acid, bromoacetic acid, peracetic acid, propionic acid, lactic acid, tartaric acid, citric acid, sorbic acid, undecenoic acid, benzoic acid; p-hydroxybenzoic acid and esters thereof, salicyclic acid, dehydracetic acid and chloroacetic acid.

2-Mercaptopyrine 1-oxide, 2-mercaptopyridine and their salts, 2,2'-dithiopyridine 1-oxide.

Quaternary ammonium compounds such as, for example, N-alkyl-N,N-dimethyl-benzylammonium chloride and di-n-decyl-dimethyl-ammonium chloride.

Guanidine derivatives such as, for example, polyhexamethylenebiguanidine hydrochloride and chlorohexidine.

Morpholine derivatives such as, for example, 4-(2-nitrobutyl)morpholine or 4,4-(2-ethyl-2-nitro-trimethylene)-dimorpholine.

Dithiocarbamates such as, for example, the salts of dimethyldithiocarbamate.

The following are preferably added as insecticides:

Phosphates such as azinphos-ethyl, azinphos-methyl, 1-(4-chlorophenyl)-4-(O-ethyl, S-propyl)phosphoryloxypyrazole, (TIA-230), chloropyrifos, coumaphos, demeton, demeton-S-methyl, diazinon, dichlorvos, dimethoate, carbamates such as aldicarb, bendiocarb, BPMC (2-(1-methylpropyl)phenyl methylcarbamate), butocarboxim, butoxicarboxim, carbaryl, carbofuran, carbosulfan, cloethocarb, isoprocarb, methomyl, oxamyl, pirimicarb, promecarb, propoxur and thiodicarb;

Pyrethroids such as allethrin, alphamethrin, bioresmethrin, byfenthrin, (FMC 54 800), cycloprothrin, cyfluthrin, decamethrion, cyhalothrin, cypermethrin, deltamethrin, alpha-cyano-3-phenyl-2-methylbenzyl-2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permethrin and resmethrin; nitroimides such as 1-[(6-chloro-3- pyridinyl)-methyl]-4,5-dihyro-N-nitro-1H-imidazol-2-anine (imidacloprid).

Other suitable active compounds are algicides, molluscicides, active compounds against "sea animals" which colonise, for example, ship's bottom paints.

The microbicidal agents or concentrates used for the protection of the industrial materials contain the active compound combinations according to the invention in a concentration of 0.01 to 95% by weight, in particular 0.01 to 60% by weight, in addition to, if appropriate, 0.001 to 10% by weight of a suitable further fungicide, insecticide or a further active compound as mentioned above.

The active compound combinations or agents according to the invention allow the previously available microbicidal agents to be replaced in an expedient manner by more effective and more environmentally-compatible agents. They show good stability and have a broad spectrum of action in an expedient manner.

The examples which follow are intended to illustrate the invention without limiting it thereto. Parts and percentages are parts by weight or per cent by weight.

The following microbicidal agents are prepared by simple mixing of the individual components.

1. 7.5 parts by weight of BHF+30 parts by weight of IPBC in 62.5 parts by weight of butyl glycol
2. 10 parts by weight of BHF+30 parts by weight of IPBC in 60 parts by weight of butyl glycol
3. 10 parts by weight of BHF+20 parts by weight of IPBC in 70 parts by weight of butyl glycol
4. 20 parts by weight of BHF+20 parts by weight of IPBC in 60 parts by weight of butyl glycol
5. 100 parts by weight of BHF+2.5 parts by weight of IPBC
6. 100 parts by weight of BHF+5 parts by weight of IPBC
7. 100 parts by weight of BHF+10 parts by weight of IPBC
8. 90.9 parts by weight of BHF+9.1 parts by weight of IPBC Use Examples A. To detect the antifungal activity, the minimum inhibitory concentrations (MICs) of agents according to the invention are determined:

An agar prepared with brewer's wort and peptone is treated with active compounds according to the invention in concentrations from 0.1 mg/l to 5000 mg/l. When the agar has solidified it is contaminated with pure cultures of the test organisms listed in Table 1. The MIC is determined after storage for 2 weeks at 28° C. and 60 to 70% relative atmospheric humidity. MIC is the lowest concentration of active compound at which no growth whatsoever of the microbe species on the agar takes place, it is given in Table 1 below.

TABLE 1

| Test organisms | MIC's in ml/l when as fungi are exposed to substances according to the invention | | | | | | | | |
|---|---|---|---|---|---|---|---|---|---|
| | Microbicidal agents in accordance with example | | | | | | | Comparison substances | |
| | 1 | 2 | 3 | 4 | 5 | 6 | 7 | BHF | IPBC |
| Alternaria tenuis | 10 | 10 | 15 | 20 | 150 | 50 | 50 | >800 | 5 |
| Aspergillus niger | 5 | 7 | 7.5 | 10 | 100 | 100 | 35 | >800 | 5 |
| Aureobasidium pullulans | 35 | 50 | 150 | 50 | 200 | 200 | 75 | >800 | 15 |
| Chaetomium globosum | 5 | 5 | 5 | 10 | 50 | 35 | 20 | 300 | 5 |
| Cladosporium herbarum | 20 | 20 | 50 | 35 | 200 | 100 | 75 | >800 | 5 |
| Penicillium brevicaule | 75 | 15 | 5 | 5 | 100 | 20 | 10 | >800 | 1 |
| Sclerophoma pityophila | 3 | 3 | 3 | 75 | 75 | 15 | 5 | 800 | 1 |
| Trichoderma viride | 50 | 50 | 50 | 50 | 400 | 200 | 200 | >800 | 10 |

B. Action against bacteria

An agar containing broth as nutrient medium is treated with microbicidal agents according to the invention in concentrations from 1 to 5000 ppm. Hereupon the nutrient medium is infected with each of the test organisms listed in Table II, and the infected medium is kept for 2 weeks at 28° C. and 60 to 70% relative atmospheric humidity. The MIC is the lowest concentration of microbicidal agent at which no growth of the microbe species used on the agar takes place. The MIC values are given in Table II

TABLE II

| | MIC values, given in mg/l, when bacteria are exposed to the active compounds below | | | | | | | | |
|---|---|---|---|---|---|---|---|---|---|
| | MIC of the microbicidal agents according to example, in ml/l | | | | | | | | |
| | 1 | 2 | 3 | 4 | 5 | 6 | 7 | BHF | IPBC |
| Escherichia coli | 800 | 400 | 800 | 800 | 400 | 400 | 400 | 700 | 100 |
| Staphylococcus aureus | 300 | 300 | 300 | 300 | 400 | 400 | 800 | 300 | 100 |
| Pseudomonas aeruginosa | >800 | >800 | >800 | >800 | 800 | 800 | 800 | 800 | >1000 |
| Pseudomonas fluorescens | >800 | >800 | >800 | >800 | 600 | 400 | 600 | 400 | >1000 |
| Bacillus subtilis | 600 | 600 | 400 | 400 | 400 | 400 | 400 | 400 | 50 |
| Aeromonas punctata | 400 | 600 | 400 | 400 | 400 | 400 | 400 | 400 | 50 |
| Proteus mirabilis | 800 | 400 | >800 | 800 | 600 | 600 | 400 | 800 | 400 |
| Leuconostoc mesanteroides | 400 | 250 | 400 | 400 | 400 | 400 | 350 | 400 | 50 |
| Aerobacter aerogenes | 250 | 400 | 400 | 400 | 400 | 250 | 100 | 400 | 50 |
| Bacillus mycoides | 100 | 100 | 400 | 100 | 400 | 400 | 400 | 400 | 50 |

C. Antimicrobial finishing of a PVAc dispersion paint of the following composition:

| Components | kg |
|---|---|
| Bayer Titan RKB2 (TiO$_2$) | 35 |
| EWO powder (BaS0$_3$) | 20 |
| Micro Mica (CaMg(C0$_3$)$_2$) | 15 |
| Talc | 5 |
| CaCO$_3$ BLP2 | 25 |
| Mowilith DM 2H (PVAc) | 80 |
| Tylose MH 2000 K-2% (CMC) | 20 |
| Calgon N 10% Polyphosphate | 2.5 |
| Pigment disperser A 10% polyacrylate | 2.5 |
| H$_2$O | 5.0 |

| Components | kg |
| --- | --- |
| | 210.0 |

Solids content: 140 kg = 66%

Samples of the abovementioned dispersion paints are treated with 0.5 to 2% of the microbicidal agent in accordance with Example 1 and tested for storage stability and mould resistance as described in the appended protocol.

Results:

If the dispersion paint contains 1.5% microbicidal agent in accordance with Example 1, it is reliably preserved; at the same time, it gives mould-resistant coatings.

In contrast, if the dispersion paint contains only IPBC (even in a larger concentration), it is not reliably preserved.

If the dispersion paint contains only BHF (even in high concentration), it is not mould resistant.

D. Preservation of a styrene/acrylate dispersion paint of the following composition:

| Components | kg |
| --- | --- |
| Bayer Titan RKB2 | 14 |
| Talc V 58 | 10 |
| Durcal 5 (CaCO$_3$) | 76 |
| Walsroder MC 3000s 2% | 35 |
| Calgon N 10% | 3 |
| Pigment disperser A 10% | 2 |
| Water | 4 |
| Nopco 8034 E (1:1 in texanol) (anti-foaming) | 1 |
| White spirit | 2 |
| Butyl diglycol acetate | 2 |
| Acronal 290 D styrolacrylate dispersion | 22 |
| | 171 |

Solids content: 111 kg = 64.3

Samples of the abovementioned dispersion paint are treated with 0.05 to 0.15% of the microbicidal agent in accordance with Example 8 and tested for storage stability in accordance with the appended protocol.

Results:

The dispersion paint is reliably preserved when it contains 0.075% of microbicidal agent in accordance with Example 8.

Test method: (mould resistance test):

Both sides of a suitable substrate are painted with the test paint.

To obtain results which are relevant to practical conditions, some of the test bodies are leached with running water (24 h; 20° C.) before they are tested for mould resistance; others are treated with a stream of warm fresh air (7 days; 40° C.).

The test bodies which have been pretreated in this manner are placed on an agar substrate. The test bodies and substrates are contaminated with fungal spores. Evaluation takes place after storage for 1 to 3 weeks at 29°±1° C. and 80 to 90% relative atmospheric humidity. The coating is permanently mould-resistant when the test body remains essentially free from fungi, or shows slight contamination at the edges at most.

Fungal spores used for the contamination are spores of the following nine moulds which are known to destroy coatings or are frequently found on coatings:
1. Alternaria tenuis
2. Aspergillus flavus
3. Aspergillus niger
4. Aspergillus ustus
5. Cladosporium herbarum
6. Paecilopmyces varioti
7. Penicillium citrinum
8. Aureobasidium pullulans
9. Stachybotrys atra Gorda Test method (in-can protection test):

To assess the in-can/in-tank protection, the preserved paints or emulsions are contaminated with bacteria and/or fungi. After a certain time, the destruction of microorganisms, or inhibition of multiplication, is assessed. The colony count is carried out on standard plate count agar 1621 (bacteria-specific) and malt extract agar 5398 (mould-specific). 1 ml of aureomycin solution is added per liter of liquid malt extract agar at a temperature of 40° to 45° C. to exclude bacterial growth.

Nutrient media:

For example standard plate count agar 1621

Malt extract agar 5398 manufactured by; E. Merck, Darmstadt

Aureomycin 0.4% strength in distilled H$_2$O manufactured by: Cyanamid GmbH

Wolfratshausen

Lederle Arzneimittel

All equipment, nutrient media and solution for dilution must be sterilised.

Procedure:

Approx. 100 g of sample are contaminated with 1 ml of a bacterial inoculum and a mould inoculum. This inoculum should contain $10^8$ to $10^9$ microorganisms per ml. Alternatively, a microbially decomposed dispersion paint can be used for contamination. The following microbe species have proved useful as test organisms:

*Staphylococcus aureus*
*Pseudomonas aeruginosa*
*Bacterium coli*
*Aspergillus niger*
*Alternaria tenuis*
*Aspergillus flavus*
*Aspergillus ustus*
*Cladosporium herbarum*
*Paecilomyces varioti*
*Penicillium citrinum*
*Aureobasidium pullulans*
*Stachybotrys atra Corda*

48 h after contamination, 1 g of paint is sampled and diluted with 20 ml of sterile, 0.85% strength saline, 1 ml of this dilution is placed in the Petri dish, and approx. 10 ml of liquid nutrient medium at a temperature of 40° to 45° C. are added.

The nutrient medium is swirled in the dish while still liquid to evenly distribute the sample. When cold, the Petri dishes are stored for 96 hours at approx. 29° C. The microbe colony-forming units (cfu) are counted after 48 and 96 h. A 20 to 40-fold magnification is sufficient for counting the colonies. The colony count is given in cfu/g of sample. If the colony count is very high, subdilutions of, for example, 1:1000 must be made to make the cfu in the Petri dish countable.

The effect of a preservative can decrease by migration of the latter from the aqueous phase to the disperse phase or by reaction with other constituents of the dispersion paint.

It is therefore advisable to carry out this test not only once immediately after the preparation of the paint but repeatedly in the course of 2 to 12 weeks. This procedure allows findings on whether the preserving action decreases with time and whether the paint in question is still resistant to contaminations at a later point in time.

An aqueous paint is well preserved if it is free from microorganisms at the end of the testing period (after 12 weeks) despite repeated severe contamination.

A sufficiently great preserving effect is also achieved when the number of introduced microorganisms is greatly reduced and the number of surviving microorganisms does not rise again in the course of 3 to 4 weeks (inhibition of microorganisms, microbistatic action).

EXAMPLE E

Preservation of mineral-oil-based cooling lubricants with BHF or IPBC on their own and in combination BHF:IPBC=100:5. Contamination with the following microorganisms which are relevant in practice:

Bacteria: Various Pseudomonas species
*Alcaligenes faecalis*
*Citrobacter freundii*
Corynebacterium
Moulds:
*Fusarium solani*
*Acremonium strictum*
*Geotrichum candidum*
Yeast:
*Rhodotorula rubra*

TABLE 3

| Perservation with | Concentration [ppm] | Bacteria per ml | Moulds per ml | Yeasts per ml |
|---|---|---|---|---|
| BHF | 200 | 0 | >$10^5$ | >$10^5$ |
| BHF | 400 | 0 | >$10^5$ | >$10^5$ |
| BHF | 800 | 0 | $10^3$ | 0 |
| BHF | 1600 | 0 | 0 | 0 |
| IPBC | 200 | >$10^5$ | 0 | 0 |
| IPBC | 400 | >$10^5$ | 0 | 0 |
| IPBC | 800 | $10^4$ | 0 | 0 |
| IPBC | 1600 | 0 | 0 | 0 |
| BHF/IPBC (100/4) | 40 | >$10^5$ | >$10^5$ | >$10^5$ |
| BHF/IPBC (100/4) | 80 | >$10^5$ | $10^3$ | $10^3$ |
| BHF/IPBC (100/4) | 160 | 0 | 0 | 0 |
| BHF/IPBC (100/4) | 200 | 0 | 0 | 0 |
| Control | — | $10^7$ | $10^5$ | $10^6$ |

It can be seen from Table 3 that approx. 1600 ppm of BHF or IPBC are required for sufficient preservation which achieves sufficient protection against attack by bacteria, moulds and yeast. In contrast, 160 ppm of the active compound mixture of BHF and IPBC in a ratio of 100:4 provide excellent protection against bacteria as well as against moulds and yeasts.

We claim:

1. A microbicidal composition for the protection of aqueous functional fluids comprising iodopropargyl N-butylcarbamate (IPBC) and benzyl alcohol mono(-poly)hemiformal (BHF).

2. A composition according to claim 1, further comprising a solvent or diluent.

3. A composition according to claim 2, further comprising an ingredient selected from the group consisting of emulsifiers, dispersants, bleaching agents or fixatives, desiccants, UV stabilizers, colors and pigments.

4. A composition according to claim 3, further comprising in addition to the IPBC another active ingredient selected from the group consisting of antimicrobial, fungicidal and insecticidal compounds.

5. A composition according to claim 1, wherein the ratio of BHF to IPBC is from about 99:1 to 50:50.

6. A composition according to claim 1, wherein the ratio of BHF to IPBC is from about 98.2 to 90:10.

7. A composition according to claim 1, wherein the ratio of BHF to IPBC is from about 40:1 to 1:4.

8. A method of protecting industrial fluids which comprises applying to such industrial fluids a microbicidal effective amount of a composition according to claim 5.

9. A method to protect industrial fluids which comprises applying to such industrial fluids a microbicidal effective amount of a mixture according to claim 1.

10. A method of protecting a paint from fungicidal attack which comprises incorporating therein a composition comprising iodopropargyl N-butylcarbamate and benzyl alcohol mono(poly)-hemiformal in a ratio from 99:1 to 50:50.

11. The method according to claim 10, wherein the composition is present in the paint in from about 0.05 to 2% by weight.

* * * * *